United States Patent
Zunker et al.

(10) Patent No.: US 6,939,289 B2
(45) Date of Patent: Sep. 6, 2005

(54) ELLIPITCAL APPLICATOR SYSTEM

(75) Inventors: Mary Ann Zunker, Oshkosh, WI (US); Herb F. Velazquez, Neenah, WI (US); Donald J. Sanders, Larsen, WI (US); Jim A. Pierron, Neenah, WI (US); Angela R. Heck, Greenville, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 10/274,855

(22) Filed: Oct. 21, 2002

(65) Prior Publication Data

US 2004/0077924 A1 Apr. 22, 2004

(51) Int. Cl.[7] ................................................ A61F 2/00
(52) U.S. Cl. ........................................ 600/29; 128/885
(58) Field of Search ....................... 600/29–32; 128/885, 128/DIG. 25, 830.841; 604/11–18, 57–60, 385.17, 904

(56) References Cited

U.S. PATENT DOCUMENTS

| | | |
|---|---|---|
| 2,355,628 A | 8/1944 | Calhoun |
| 2,739,593 A | 3/1956 | McLaughlin |
| 3,032,036 A | 5/1962 | Rader et al. |
| 3,204,635 A | 9/1965 | Voss et al. |
| 3,409,011 A | 11/1968 | Mittag |
| 3,643,661 A | 2/1972 | Crockford |
| 3,765,417 A | 10/1973 | Crockford |
| 3,766,921 A | 10/1973 | Dulle |
| 3,918,452 A | 11/1975 | Cornfeld |
| 3,971,378 A | 7/1976 | Krantz |
| 4,019,498 A | 4/1977 | Hawtrey et al. |
| 4,198,978 A | 4/1980 | Nigro |
| 4,212,301 A | 7/1980 | Johnson |
| 4,286,594 A | 9/1981 | Cunningham |
| 4,312,348 A | 1/1982 | Friese |
| 4,318,404 A | 3/1982 | Cunningham |
| 4,318,405 A | 3/1982 | Sneider |
| 4,398,532 A | 8/1983 | Sweeney, III |

(Continued)

FOREIGN PATENT DOCUMENTS

| | | |
|---|---|---|
| DE | 1815375 | 9/1970 |
| EP | 0104039 A1 | 3/1984 |
| EP | 0610951 A1 | 8/1994 |
| EP | 0749741 B1 | 12/1996 |
| GB | 1116742 | 6/1968 |
| WO | WO 95/13041 | 5/1995 |
| WO | WO 97/01318 | 1/1997 |
| WO | WO 00/37012 | 6/2000 |
| WO | WO 00/67662 | 11/2000 |
| WO | WO 02/26159 A1 | 4/2002 |
| WO | WO 02/056793 A2 | 7/2002 |

*Primary Examiner*—John P. Lacyk
(74) *Attorney, Agent, or Firm*—Brinks Hofer Gilson & Lione; G. Peter Nichols

(57) ABSTRACT

An applicator for placing an insert within a vagina. The insert can be a catamenial tampon, incontinence device, medicament, dressing, and the like. The applicator has orientation indicators to allow the user to properly orientate the insert within the vagina. The applicator also has an inwardly curved radius on the leading edge to reduce any resistance during insertion and withdrawal of the applicator. The applicator may also have at least one vent to facilitate expulsion of the insert or to deliver medicaments or lubricants inside the body cavity. The insert applicator has a rounded cross-section to maximize the available space for the insert, while also facilitating insertion of the applicator into the vagina.

17 Claims, 3 Drawing Sheets

U.S. PATENT DOCUMENTS

| | | |
|---|---|---|
| 4,421,504 A | 12/1983 | Kline |
| 4,424,054 A | 1/1984 | Conn et al. |
| 4,498,899 A | 2/1985 | Gross |
| 4,536,178 A | 8/1985 | Lichstein et al. |
| 4,573,963 A | 3/1986 | Sheldon |
| 4,573,964 A | 3/1986 | Huffman |
| 4,690,671 A | 9/1987 | Coleman et al. |
| 4,857,044 A | 8/1989 | Lennon |
| 4,921,474 A | 5/1990 | Suzuki et al. |
| 5,036,867 A | 8/1991 | Biswas |
| 5,080,659 A | 1/1992 | Nakanishi |
| 5,267,953 A | 12/1993 | Paul et al. |
| 5,395,308 A | 3/1995 | Fox et al. |
| 5,395,309 A | 3/1995 | Tanaka et al. |
| 5,437,628 A | 8/1995 | Fox et al. |
| 5,533,990 A | 7/1996 | Yeo |
| 5,542,914 A | 8/1996 | Van Iten |
| 5,554,109 A | 9/1996 | Frayman |
| 5,603,685 A | 2/1997 | Tutrone, Jr. |
| 5,618,256 A | 4/1997 | Reimer |
| 5,659,934 A | 8/1997 | Jessup et al. |
| 5,709,652 A | 1/1998 | Hagerty |
| 5,755,906 A | 5/1998 | Achter et al. |
| 5,785,640 A | 7/1998 | Kresch et al. |
| 5,795,346 A | 8/1998 | Achter et al. |
| 5,873,971 A | 2/1999 | Balzar |
| 5,988,386 A | 11/1999 | Morrow |
| 6,019,743 A | 2/2000 | Cole et al. |
| 6,039,716 A | 3/2000 | Jessup et al. |
| 6,039,828 A | 3/2000 | Achter et al. |
| 6,056,714 A | 5/2000 | McNelis et al. |
| 6,071,259 A | 6/2000 | Steiger et al. |
| 6,090,038 A | 7/2000 | Zunker et al. |
| 6,090,098 A | 7/2000 | Zunker et al. |
| 6,095,998 A | 8/2000 | Osborn, III et al. |
| 6,142,928 A | 11/2000 | Zunker et al. |
| 6,196,988 B1 | 3/2001 | Cole et al. |
| 6,248,089 B1 | 6/2001 | Porat |
| 6,270,470 B1 | 8/2001 | Buck et al. |
| 6,645,136 B1 * | 11/2003 | Zunker et al. ................ 600/29 |

* cited by examiner

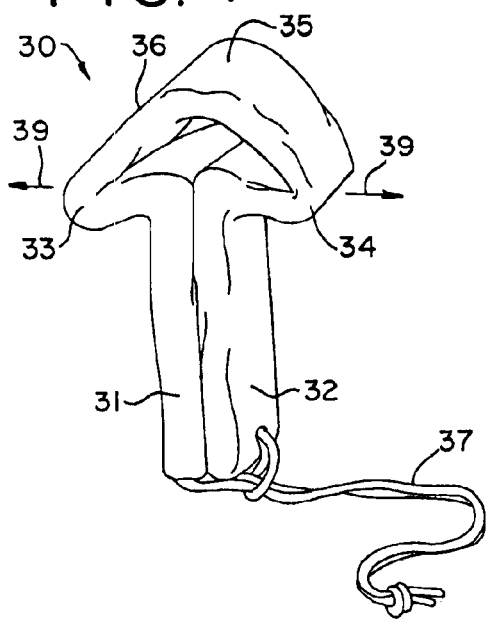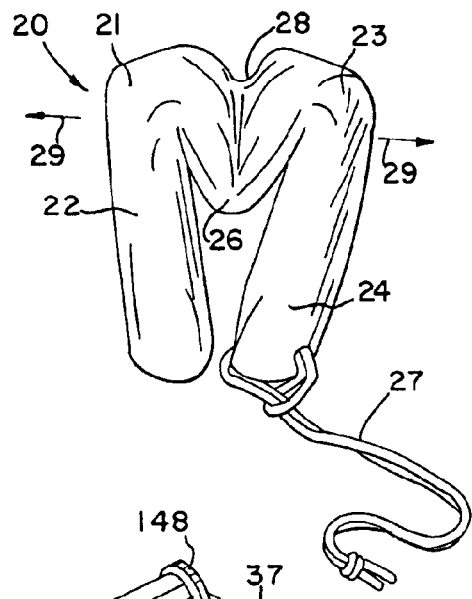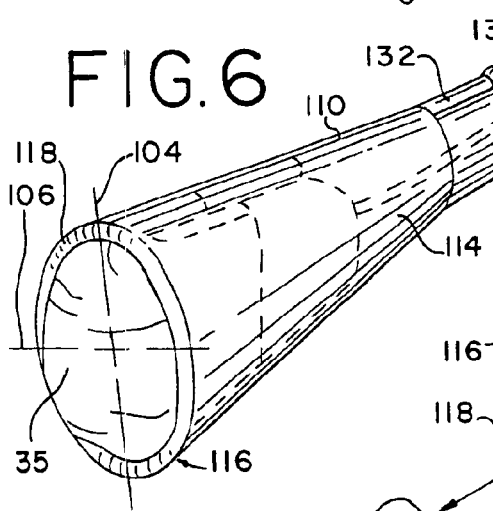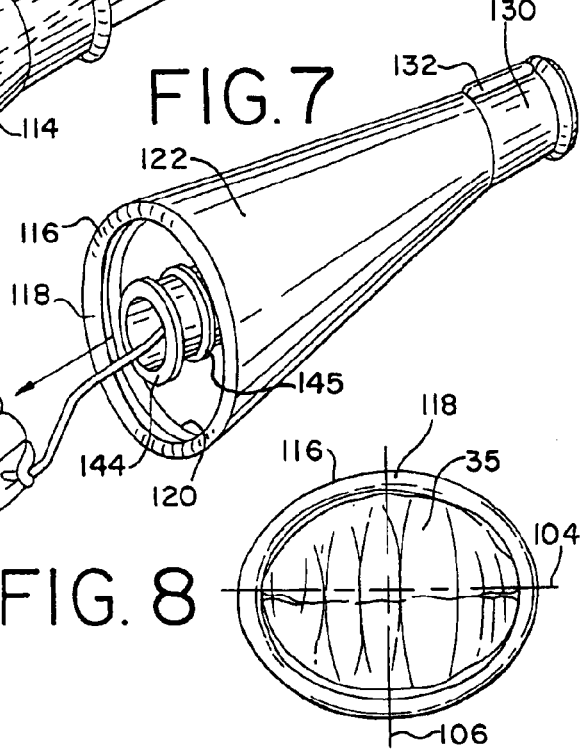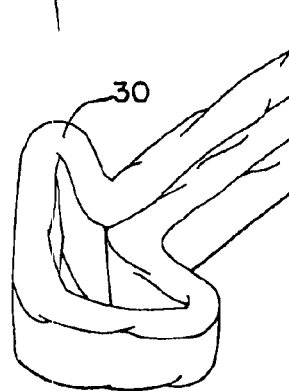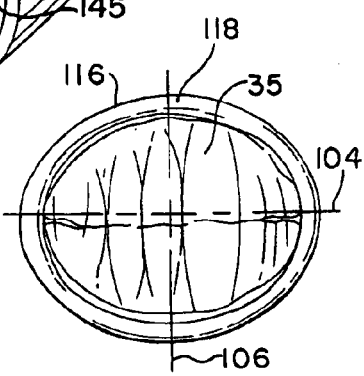

ELLIPITCAL APPLICATOR SYSTEM

FIELD OF THE INVENTION

The present invention relates generally to devices for delivering an insert into a body cavity, particularly a vagina and to methods for their use. The insert may be a catamenial tampon, incontinence device, medicament, dressing, or other similar inserts. The invention may find particular use for delivering inserts used to reduce the occurrence and/or severity of female urinary incontinence. More particularly, the present invention relates to an improved carriage for an applicator for delivering an incontinence device.

BACKGROUND OF THE INVENTION

Some women, especially women who have given birth to one or more children, and older women, can experience incidences of involuntary urine loss due to stress urinary incontinence or combined stress and urge incontinence. Accordingly, as the world's female population ages, there is an ever increasing need for a non-surgical procedure and/or device to reduce the involuntary urine loss commonly associated with "stress urinary incontinence." One way to alleviate the problem of incontinence is to place an insert within the vagina to allow the urethra to compress and/or provide support for the bladder neck in order to prevent the involuntary loss of urine. Inserts developed for such purposes are disclosed in U.S. Pat. Nos. 6,090,038; 6,090,098; 6,142,928; U.S. application Ser. No. 09/675,459; and in U.S. application Ser. No. 09/675,460.

One challenge associated with the use of the inserts of the above mentioned patents and applications is that they are most effective when properly oriented within the vagina. Furthermore, because the inserts are relatively large compared to other vaginally inserted devices, such as catemenial tampons, there is a challenge making a device that can properly place the inserts within the vagina without causing discomfort. One solution is disclosed in commonly assigned, co-pending U.S. Ser. No. 09/675,458, which shows an elliptical applicator. While this applicator is suitable for its intended use, the applicator of the present invention improves upon that device.

In addition, another problem associated with the use of inserts is that they may be difficult to eject from the applicator, which may result in unnecessary discomfort experienced by the user. Therefore, it would be desirable to provide an applicator in which the insert may be easily ejected from the applicator. The applicator of the present invention solves this problem by providing vents that reduce the friction between the insert and the inner surface of the applicator. As a result, the insert is more easily ejected from the applicator.

SUMMARY OF THE INVENTION

In one aspect of the present invention, an insert applicator includes an outer member adapted to house an insert, and an inner member moveable within the outer member and operable to discharge the insert from the outer member. The leading, vaginal insertion end portion of the outer member has an inwardly curved radius. The insert applicator may also be provided with at least one vent on the outer member that will reduce the friction between the insert and the inner surface of the outer member and will also aid in the expulsion of the insert from the applicator.

In another aspect of the invention, a device is provided that includes an insert and an applicator. The applicator includes an outer member adapted to house the insert and an inner member moveable within the outer member and operable to discharge the insert out of an exit portion of the outer member. The outer member is substantially cone-shaped and has a wider cross-section at the insert exit portion that has an inwardly curved radius to present a smooth surface to reduce friction during insertion of the device. The applicator may also be provided with at least one vent on the outer member that will reduce the friction between the insert and the inner surface of the outer member. The vents will also aid in the expulsion of the insert from the outer member or carriage.

In another aspect of the invention, a device is provided for reducing the occurrence and/or severity of female urinary incontinence. The device includes an insert and an applicator. The applicator includes an outer member adapted to house the insert and an inner member moveable within the outer member and operable to discharge the insert from an exit portion of the outer member. The outer member has an inwardly curved radius at the leading or vaginal insertion end.

Other aspects of the invention will be apparent to those of skill in the art in view of the appended claims.

BRIEF DESCRIPTION OF THE DRAWINGS

FIG. 4 is a view of one embodiment of an insert that can be used with the applicators of the present invention.

FIG. 5 is a view of another embodiment of an insert that can be used with the applicators of the present invention.

FIG. 6 is a perspective view of one embodiment of the applicator of the present invention that shows an insert in phantom and in a position to be delivered.

FIG. 7 is a perspective view of the applicator shown in FIG. 6 that shows the insert discharged from the applicator.

FIG. 8 is a front view of one embodiment of the applicator of the present invention where the applicator has an elliptical shape.

DESCRIPTION OF THE INVENTION

Figure 1:
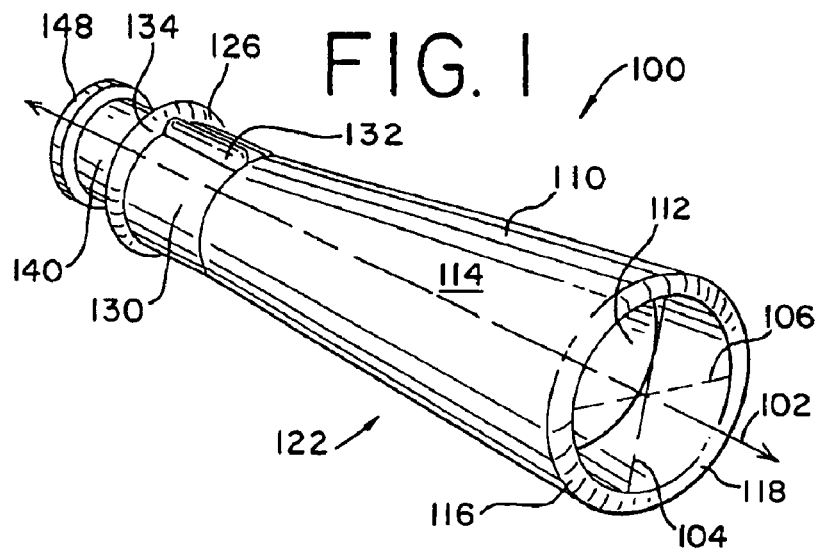
FIG. 1 is a perspective view of one embodiment of the applicator according to the present invention.

Referring now to the drawings and initially to FIG. 1, an insert applicator according to the present invention is shown generally at 100 in a pre-assembled configuration. The applicator 100 has an outer member or insert housing (or carriage) 110 and an inner member or plunger 140. The inner member 140 is slidably disposed within the outer member 110. The outer member 110 has a curved shape such as a cylinder, particularly a circle or ellipse and has an inner surface 112 and an outer surface 114. The outer member 110 extends along a longitudinal axis 102 from a leading, vaginal insertion end portion 116 to a trailing end portion 126. The outer member 110 houses an insert (not shown) that is to be discharged into the vaginal cavity.

Desirably, the outer member 110 includes a substantially cone-shaped portion 122 and a substantially cylindrical-shaped portion 130 extending substantially parallel to the longitudinal axis 102. In a direction substantially parallel to its longitudinal axis, the cone-shaped portion 122 and the cylindrical portion 130 may have the same shape or may have different shapes. For example, both may have a substantially circular, or oval or elliptical cross-section. Preferably, the cone-shaped portion is oval or elliptical.

The outer member 110 and, in particular, the vaginal insertion end portion 116 has a major axis 104 and a minor axis 106. In one embodiment as shown in FIG. 1, the major axis 104 and the minor axis 106 are nearly equal. In other words, in this embodiment, the cross-section of the vaginal insertion end portion 116 of the outer member 110 is almost circular. In another embodiment, best illustrated in FIG. 8, the major axis 104 is defined by the longest diameter of the cross-section and the minor axis 106 is defined by the shortest diameter of the cross-section. In other words, in this embodiment, the cross section of the vaginal insertion end portion 116 of the outer member 110 is substantially elliptical. An elliptical shape is preferred because it more closely resembles the shape of the vagina and therefore, will be more easily inserted into and removed from the vagina.

The cone-shaped portion 122 has a wider cross-section at the vaginal insertion end 116, and a smaller cross-section connected with the cylindrical portion 130. The vaginal insertion end portion 116 of the outer member 110 has an inwardly curved radius 118 to provide a continuous surface and a smooth reduced friction surface. In other words, the leading edge 116 of the outer member 110 is inwardly curved such that the leading edge is the apex of the outer member. The inwardly curved radius 118 ranges from about 0.005 to about 0.05 inches, preferably from about 0.01 to about 0.03 inches. The inwardly curved radius 118 extends into the inner surface 112 of the outer member 110 where it stops to define a flange 120 on at least a portion of the circumference of the inner surface 112 of the outer member 110. The flange 120 helps to maintain the insert 20, 30 within the outer member 110 until its discharge into the vagina.

The cylindrical shaped portion 130 defines a gripping portion for the outer member 110. The cylindrical portion 130 terminates at the trailing end 126, which is provided with an outer flange 134 that extends at least a portion of the circumference of the trailing end 126 to provide a gripping surface for the outer member 110. Preferably, the outer flange 134 extends the entire circumference of the trailing end 126.

The trailing end 126 may also be provided with an inner flange 136 that surrounds at least a portion of the inner surface 112 of the outer member 110. The inner flange 136 is located in the cylindrical shaped portion 130 and may be located in the same plane as the outer flange 134 or may be located in a different plane. The inner flange 136 will act as a stop for the inner member 140.

The applicator 100 may also include one or more orientation indicators 132. In the embodiment shown in FIG. 1, the orientation indicator 132 is in the form of a raised rib that extends parallel to the longitudinal axis 102 of the applicator 100. The orientation indicator 132 is located on the outer surface of the outer member 110 and is desirably located on the cylindrical shaped portion 130. The orientation indicator 132 is positioned to indicate the relative rotational position of the applicator 100, and therefore, allows the user to correctly orient the insert 20, 30 inside the vagina, as more fully described below.

In one embodiment where the applicator 100 is elliptical as shown in FIG. 6, the orientation indicator 132 is located on the major axis 104 of the elliptical cross-section of the outer member 100. In this embodiment, an orientation indicator 132 is located on each major axis 104 opposite each other and on the cylindrically shaped portion 130. Alternatively, the orientation indicator 132 may be located on the minor axis 106.

The applicators of the present invention should be made of a biocompatible material, such as a paperboard stock, or a plastic. The outer member 110 is preferably about 50 to 75 mm in length, more preferably about 60 to 70 mm, and most preferably about 65 mm. The major axis of the elliptical cross-section is preferably about 20 to 40 mm in length, more preferably about 25 to 35 mm, and most preferably about 30 mm. The minor axis of the elliptical cross-section is about 10 to 30 mm in length, more preferably about 10 to 20 mm, and most preferably about 15 mm. The inner member 150 is preferably about 50 mm to about 100 mm in length, more preferably about 65 to 85 mm, and most preferably about 75 mm.

Various modifications may be made to the applicators shown without departing from the scope of the present invention. For example, while it is preferred that the orientation indicators 132 are located on the minor axis 106 of the elliptical cross-section of the outer member 110, the orientation indicators 132 may alternately be placed on other areas of the outer member 110, as well as on the inner member 140. The orientation indicators 132 may also be significantly larger than those shown. In addition, while the orientation indicators 132 have been shown as tabs, the orientation indicators 132 may be formed of other structures or by indicia such as marks or the like.

Furthermore, although the applicators in some embodiments have a substantially elliptical cross-section for the entire longitudinal length of both the outer member 110 and the inner member 140, some applicators within the scope of the invention may have a substantially elliptical cross-section for less than the entire longitudinal length of either the outer member and/or the inner member. In the preferred embodiments, the applicators will have a substantially elliptical cross-section at least at the leading, vaginal insertion end 116 portion of the outer member 110, with the option of having a more conventional or circular cross-section the rest of the length. In more preferred embodiments, the applicators will have a substantially elliptical cross-section for a substantial portion of the longitudinal length of the outer member 110 and/or inner member 140. In even more preferred embodiments, the applicators will have a substantially elliptical cross-section for at least half the longitudinal length, and in even more preferred embodiments, the substantially elliptical cross-section will extend at least three-quarters the longitudinal length of the outer member 110 and/or inner member 140. In the most preferred embodiment, the applicators will have a substantially elliptical cross-section for substantially the entire length of the outer member 110 and/or inner member 140.

As noted above, the inner member 140 is sized and shaped to be slidably disposed within the outer member 110 and to share the common longitudinal axis 102 as the outer member 110. The inner member 140 is operable to discharge the insert 20, 30 into the vagina when the applicator 100 is inserted into the vagina. The inner member 140 has a shaft 142 that connects a head portion 144 and a trailing end 146, which is provided with a flange 148 located about a substantial portion of the circumference of the trailing end 146 to provide a gripping surface.

The head portion 144 is in contact with the insert 20, 30 while the insert 20, 30 is disposed within the outer member 110. The head portion 144 operates to discharge the insert 20, 30 from the outer member 110. The inner member flange 148 will contact the outer member flange 134 provided on the cylindrically shaped portion 130 of the outer member 110 when the inner member 140 is pushed forward (i.e., in a direction from the trailing end 126 toward the vaginal insertion end 116) to discharge the insert 20, 30. In addition, the head portion 144 is provided with a head flange 145 that will contact the inner flange 136 provided on the inner surface 112 of the outer member 110 to act as a stop for the inner member 140 so that the inner member 140 cannot be removed from the outer member 110.

Figure 2:
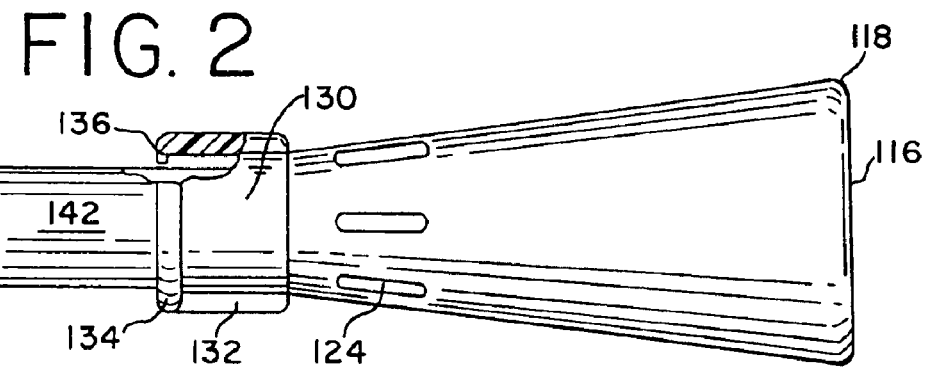
FIG. 2 is a side elevation of another embodiment of the applicator according to the present invention that shows vents located near one end of the applicator.
Figure 3:
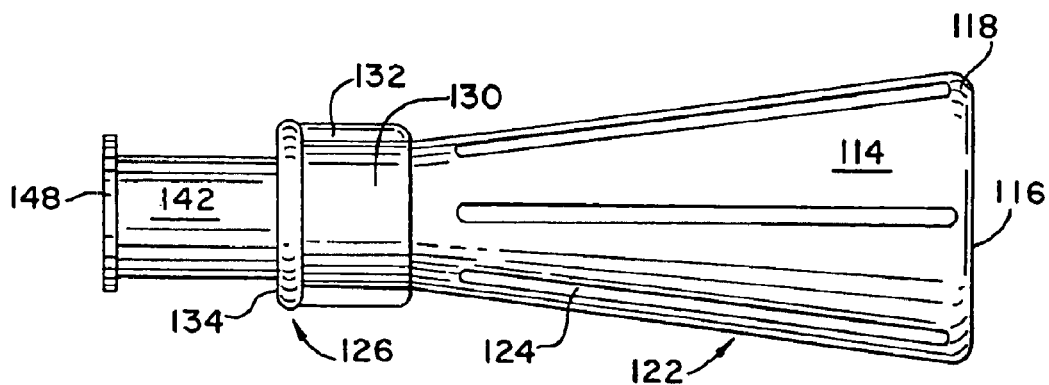
FIG. 3 is a side elevation of another embodiment of the applicator according to the present invention that shows vents along a substantial portion of the cone shaped portion of the applicator.

Turning now to FIGS. 2 and 3, an alternate embodiment of the insert applicator 100 according to the present invention is shown in a pre-assembled configuration. In this embodiment, the applicator 100 is the same as that described above with respect to FIG. 1, but it includes at least one vent 124 provided on the outer member 110.

The at least one vent 124 is preferably placed on the cone shaped portion 122 adjacent the substantially cylindrical-shaped portion 130. Preferably, a plurality of vents 124 are spaced about the circumference of the outer member 110. The vents 124 may take any shape but are generally shaped to provide a major axis parallel to the longitudinal axis 102. The vents 124 reduce the friction experienced by the insert 20, 30 against the inner surface 112 of the outer member 110. In addition, the vents 124 will aid in the expulsion of the insert 20, 30 during discharge of the insert 20, 30 into the vagina. Moreover, the vents 124 will likely be useful in delivering drugs, medicaments, lubricants and the like as the inner member 140 pushes the insert 20, 30 out the vaginal insertion end 116 of the outer member.

Referring more particularly to FIG. 3, the vents 124 are shown as extending from the cylindrically shaped portion 130 a substantial distance toward the vaginal insertion end 116. Accordingly, one skilled in the art will understand that the vents can have any suitable length as illustrated in FIGS. 2 and 3.

FIGS. 4 and 5 illustrate inserts in the form of an incontinence insert that can be delivered using the applicator of the present invention. An "incontinence insert" as used herein refers to devices specifically designed, configured, and/or adapted for placement into a vagina in order to reduce the occurrence and/or severity of female urinary incontinence. While incontinence inserts are typically made of non-absorbent materials, at least partially absorbent materials may also be used. There is, however, no advantage to using absorbent materials because there is no intent to absorb any bodily fluids. Therefore, incontinence inserts are readily distinguishable from catamenial tampons. Nevertheless, one skilled in the art will understand that the applicator of the present invention may be useful in delivering catamenial tampons, medicaments, and the like.

In FIG. 5, an insert having an "M-shape" profile in a plane parallel to the directions indicated by arrows 29 is shown generally at 20. Such inserts are more fully disclosed in U.S. Pat. No. 6,142,928; U.S. application Ser. Nos. 09/675,459 and 09/675,460, all of which are incorporated herein by reference in their entireties. Briefly, the insert 20 is formed from an elongated member having a first end portion 22 and a second end portion 24, and has three folds, 21, 23, and 26. The first end portion 22 and the second end portion 24 are aligned generally adjacent each other and, together with the folds 21, 23, 26, form a generally planar M-shaped profile. An inward crease 28 is formed in a direction generally perpendicular to the plane of the M-shaped profile. One of the end portions is attached to a withdrawal member, such as a string 27. The insert 20 preferably includes, or is predominately made from, a resilient material that functions to expand the insert 20 in at least a direction indicated by arrows 29 once the insert 20 is placed within the vagina.

In order for the insert 20 to be most effective in reducing the occurrence and/or severity of incontinence, the insert 20 should be properly placed and correctly oriented within the vagina. Specifically, the insert 20 should expand in the direction 29 so as to press against and/or compress the urethra and support the urinary sphincter muscle, thereby reducing the occurrence and/or severity of incontinence, as more fully described in U.S. Pat. No. 6,142,928. The applicators of the present invention help provide this correct orientation of the insert, as described above with reference to FIGS. 1–3 and 6–7.

To correctly orient the insert 20, the user simply discharges the insert in a position so that it expands in a direction indicated by arrow 29 (FIG. 5) towards the urethra and provides support to the urinary sphincter muscle. This can be accomplished simply by discharging the insert 20 only when the applicator 100, having been inserted into the vagina, is oriented such that an imaginary line connecting the two orientation indicators 132 are substantially perpendicular with the major axis of the opening of the vagina. As used herein, the major axis of the opening of the vagina is defined as the axis across the opening of the vagina generally extending in direction from the prepuce of the clitoris to the fourchet and/or the anal opening. The correct orientation is accomplished by rotating the applicator 100 ninety degrees in either direction after insertion of the applicator 100 into the vagina but before expulsion of the insert.

Those skilled in the art will recognize that the applicator 100 is also useful with the insert 30 shown in FIG. 4, as well other inserts. Those skilled in the art will also appreciate that various modifications may be made to the incontinence inserts shown. For example, the manners of attachment of the withdrawing member shown in FIGS. 4 and 5 are only exemplary, and other manners known in the art can be used equally as well. While various modifications may be made to the inserts shown, the advantages of the applicator 100 are most apparent and fully realized where the effective functioning of the insert is at least in part dependent upon its correct orientation within the vagina, as is the case for the inserts of FIG. 4 and FIG. 5.

FIGS. 9A–9D illustrate cross-sections of alternate embodiments of the applicators of the present invention. As previously mentioned, the most preferred applicators have substantially elliptical cross-sections in at least in their leading, vaginal insertion end portions, in order to accurately approximate the shape of the opening of the vagina, thereby facilitating the insertion of the applicator, while also maximizing the space available for housing an insert. Other cross-sections, while perhaps not facilitating the insertion process as well as a substantially elliptical cross-section, are advantageous nevertheless to maximize the space for housing a particular insert, such as an insert having an asymmetrical shape.

Figure 9A:
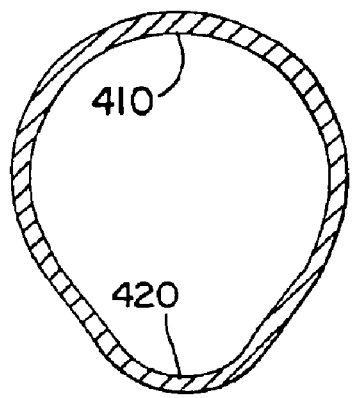
FIGS. 9A–9D are cross sectional views of alternate embodiments of the applicator according to the present invention.

FIG. 9A illustrates an alternate embodiment of the applicators having non-circular cross-section according to the present invention. The cross-section is substantially "egg-shaped," that is, one portion 410 of the cross-section is substantially circular in contour, and another portion 420, continuous with the substantially circular portion 410, is substantially elliptical in contour.

Figure 9B:
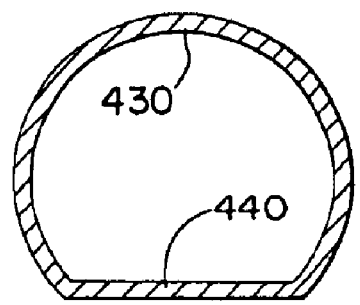

FIG. 9B illustrates another alternate cross-section for the applicators of the present invention. The cross-section includes one portion 430 that is substantially circular in contour, and another portion 440, continuous with the substantially circular portion 430, is substantially flat or straight.

Figure 9C:
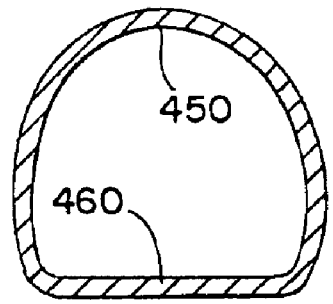

FIG. 9C illustrates a third alternate cross-section for the applicators of the present invention. The cross-section includes one portion 450 that is substantially elliptical in contour, and another portion 460, continuous with the substantially elliptical portion 450, is substantially flat or straight.

Figure 9D:
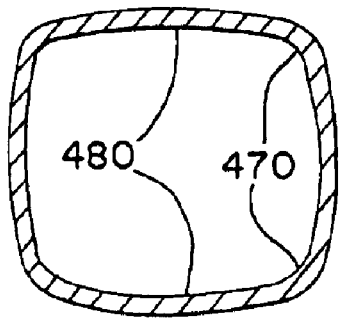

FIG. 9D illustrates a fourth alternate cross-section for the applicators of the present invention. The cross-section is defined herein as a "soft-square," that is, the cross-section is substantially a square. Its corners 470 and/or the sides 480, however, are slightly or softly curved. Other slightly curved quadrilaterals may also be used may for the cross-sections, such as soft-rectangles and soft-trapezoids.

Like the substantially elliptical cross-sections, the alternate cross-sections of FIGS. 9A–9D are shown in a direction substantially perpendicular to the longitudinal axis of the applicator. Furthermore, the alternate non-circular cross-sections of FIGS. 9A–9D need not extend the entire length of the applicator, but rather may be combined with other cross-sections. The preferred alternate embodiments of the applicators will have the cross-sections of any of FIGS. 9A–9D at least at the leading, vaginal insertion end portion of the outer member. In more preferred embodiments, the applicators will have one of the alternate cross-sections for a substantial portion of the longitudinal length of the outer member and/or inner member. In even more preferred embodiments, the applicators will have an alternate cross-section for at least half the longitudinal length, and in even more preferred embodiments, the alternate cross-section will extend at least three-quarters the longitudinal length of the outer member and/or inner member. In the most preferred embodiment, the applicators will have an alternate cross-section for substantially the entire length of the outer member and/or inner member.

According to another aspect of the present invention, a method is provided for properly positioning an insert within a vagina so that the insert is effective in reducing the occurrence and/or severity of involuntary urine loss. The method uses an insert applicator according to the present invention. Specifically, the preferred applicators useful in the method have a curved cross section, such as an elliptical cross-section, or one of the cross-sections shown in FIGS. 9A–9D.

In one embodiment of the method, the applicator is inserted into the vagina such that the major axis of the substantially elliptical cross-section of the applicator is substantially parallel with the major axis of the opening of the vagina. The applicator is inserted and advanced into the vagina until either the fingers of the user that are holding the gripping portion of the applicator are resting against the body, or until the gripping portion is flush with the vaginal opening. Typically, the applicator is advanced approximately 2 to 3 inches. After inserting the applicator, the applicator is rotated about 90 degrees such that the minor axis of the elliptical cross-section is substantially perpendicular with the major axis of the opening of the vagina. The insert is then discharged into the vagina in its proper orientation.

In an alternate embodiment, where the applicators have orientation indicators, the applicator is oriented based upon the orientation indicators. Preferably, the applicator is first inserted into the vagina, and then oriented by rotation based upon the orientation indicators. Alternatively, the applicator may be oriented before insertion based upon the orientation indicators, so that the applicator is correctly oriented when inserted. The insert is then discharged into the vagina in its correct orientation.

While the invention has been described in conjunction with specific embodiments, it is to be understood that many alternatives, modifications, and variations will be apparent to those skilled in the art in light of the foregoing description. Accordingly, this invention is intended to embrace all such alternatives, modifications, and variations that fall within the spirit and scope of the appended claims.

What is claimed:

1. A vaginal incontinence device applicator comprising:
   a. an outer member having a longitudinal axis extending from a leading vaginal insertion end portion to a trailing end portion, wherein the vaginal insertion end portion of the outer member has a non-circular cross-section in a direction substantially perpendicular to the longitudinal axis and wherein the vaginal insertion end portion is inwardly curved to provide a smooth exterior surface and to define a flange on an inner surface of the outer member;
   b. at least one vent provided on the outer member wherein the at least one vent extends parallel to the longitudinal axis from adjacent the trailing end to adjacent the vaginal insertion end; and,
   c. an inner member longitudinally moveable within the outer member.

2. The applicator of claim 1 wherein the vaginal insertion end portion has a substantially elliptical cross-section.

3. The applicator of claim 2 wherein the trailing end portion has a substantially circular cross section.

4. The applicator of claim 3 further comprising at least one orientation indicator provided on the outer member and indicating a major axis of the elliptical cross-section.

5. The applicator of claim 1 further comprising at least one flange provided around at least a portion of the circumference of the trailing end portion of the outer member and extending forward.

6. The applicator of claim 1 further comprising at least one flange provided on at least a portion of an inner surface of the trailing end portion of the outer member.

7. The applicator of claim 6 wherein the inner member comprises a shaft connecting a head portion and a trailing end; wherein an inner flange is provided adjacent the head portion such that when the inner member is selectively positioned with respect to the outer member, the flange on the inner member contacts the inner flange.

8. An insert applicator comprising:
   a. an outer member having a longitudinal axis extending from a trailing end portion to a leading vaginal insertion end portion having an elliptical cross section and an inwardly curved radius to define a flange on an inner surface of the outer member, wherein the outer member is adapted to house an insert;
   b. at least one vent provided on the surface of the outer member wherein the at least one vent extends parallel to the longitudinal axis from adjacent the trailing end to adjacent the vaginal insertion end; and
   c. an inner member longitudinally moveable with the outer member and operable to discharge the insert from the outer member.

9. The insert applicator of claim 8 wherein the outer member comprises a cone-shaped portion extending substantially parallel to the longitudinal axis.

10. The insert applicator of claim 9 further comprising a cylinder connected with a smaller end of the cone-shaped portion of the outer member, wherein the inner member slideably engages an inner surface of the cylinder.

11. The insert applicator of claim 10, further comprising at least one orientation indicator provided on the outer member and indicating a major axis of the elliptical cross section.

12. The insert applicator of claim 11 further comprising at least one flange provided around at least a portion of the circumference of the trailing end portion of the outer member and extending forward.

13. The applicator of claim 12 further comprising at least one flange provided on at least a portion of an Inner surface of the trailing end portion of the outer member.

14. The applicator of claim 13 wherein the inner member comprises a shaft connecting a head portion and a trailing end, wherein an inner flange is provided adjacent the head portion such that when the inner member is selectively positioned with respect to the outer member, the flange on the inner member contacts the inner flange of the outer member.

15. A vaginal incontinence device applicator comprising:
  a. an outer member having a longitudinal axis extending from a leading vaginal insertion end portion to a trailing end portion, wherein the vaginal insertion end portion is inwardly curved to provide a smooth exterior surface and to define a flange on an inner surface of the outer member;
  b. at least one vent provided on the surface of the outer member wherein the at least one vent extends parallel to the longitudinal axis from adjacent the trailing end to adjacent the vaginal insertion end; and
  c. an inner member longitudinally moveable within the outer member.

16. The applicator of claim 15 wherein the vaginal insertion end portion of the outer member has a non-circular cross-section in a direction substantially perpendicular to the longitudinal axis.

17. A vaginal incontinence device applicator comprising:
  a. an outer member having a longitudinal axis extending from a leading vaginal insertion end portion to a trailing end portion;
  b. at least one vent provided on the outer member wherein the at least one vent extends parallel to the longitudinal axis from adjacent the trailing end to adjacent the vaginal insertion end; and
  c. an inner member longitudinally moveable within the outer member.

* * * * *